United States Patent [19]

Zambounis

[11] Patent Number: 5,281,730
[45] Date of Patent: Jan. 25, 1994

[54] SUBSTITUTED TETRACYANOQUINODIMETHANES, PROCESSES FOR THEIR PREPARATION AND THEIR USE

[75] Inventor: John Zambounis, Murten, Switzerland

[73] Assignee: Ciba-Geigy Corporation, Ardsley, N.Y.

[21] Appl. No.: 48,084

[22] Filed: Apr. 15, 1993

[30] Foreign Application Priority Data

Apr. 22, 1992 [CH] Switzerland ............ 1305/92

[51] Int. Cl.$^5$ ............ C07C 50/06; C07C 323/09
[52] U.S. Cl. .................... 552/303; 568/56
[58] Field of Search .................... 552/303

[56] References Cited

U.S. PATENT DOCUMENTS 4,758,381 7/1988 Suga et al. .................... 552/303

FOREIGN PATENT DOCUMENTS 62-26260 4/1987 Japan .................... 552/303

OTHER PUBLICATIONS

Wheland, et al., J. Org. Chem., 40(1975), pp. 3101–3109.
Wheland, et al., J.A.C.S., 98(19876), pp. 3916–3925.
Hiroyoshi, et al., C.A., 92(1980), 92:59385g.

Primary Examiner—Joseph Paul Brust
Attorney, Agent, or Firm—Kevin T. Mansfield; George R. Dohmann

[57] ABSTRACT

Compounds of the formula I

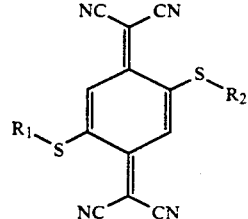

in which $R_1$ and $R_2$ independently of one another are $C_1$–$C_6$alkyl, $C_3$–$C_8$cycloalkyl which is unsubstituted or substituted by $C_1$–$C_4$alkyl, or phenyl or benzyl which is unsubstituted or substituted by F, Cl, Br, $C_1$–$C_6$alkyl, $C_1$–$C_6$alkoxy or di($C_1$–$C_6$alkyl)amino.

The compounds are suitable as π-acceptors and electrical semiconductors, and they can be used for antistatic finishing of objects.

5 Claims, No Drawings

SUBSTITUTED TETRACYANOQUINODIMETHANES, PROCESSES FOR THEIR PREPARATION AND THEIR USE

The present invention relates to 1,4-tetracyanoquinodimethanes which are substituted by organic thio radicals in the 2,5-positions, a process for their preparation and their use, and, as an intermediate of the process, to 1,4-di-(chloromethyl)-phenyl substituted by organic thio radicals in the 2,5-positions.

R. C. Wheland and E. L. Martin described tetracyanoquinodimethanes (abbreviated to TCNQ below), for example TCNQ (O-ethyl)(S-methyl), and anionic salts thereof in J. Org. Chem. Volume 40, No. 21, pages 3101–9 (1975). It is known, for example described by R. C. Wheland et al. in J. Am. Chem. Soc. 98, p. 3916-25 (1976) that unsubstituted and substituted TCNQ electron acceptors can be used for electrically conductive charge transfer (CT) complexes. TCNQs which are in themselves electrical conductors or semiconductors are not yet known.

It has now been found, suprisingly, that 1,4-tetracyanoquinodimethanes which are substituted by organic thio radicals in the 2,5-positions are in themselves electrical semiconductors when in the form of layers on a carrier material.

The invention relates to compounds of the formula I

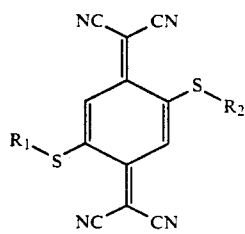

in which $R_1$ and $R_2$ independently of one another are $C_1$–$C_6$alkyl, $C_3$–$C_8$cycloalkyl which is unsubstituted or substituted by $C_1$–$C_4$alkyl, or phenyl or benzyl which is unsubstituted or substituted by F, Cl, Br, $C_1$–$C_6$alkyl, $C_1$–$C_6$alkoxy or di($C_1$–$C_6$alkyl)amino. $R_1$ and $R_2$ are preferably identical radicals.

Alkyl $R_1$ and $R_2$ can be linear or branched and preferably contain 1 to 4 C atoms. Examples are methyl, ethyl, n- and i-propyl, n-, i- and t-butyl, pentyl and hexyl. Preferred alkyl radicals are methyl and ethyl.

Examples of cycloalkyl are cyclopropyl, cyclopentyl, cyclohexyl, cycloheptyl and cyclooctyl. Preferred cycloalkyl radicals are cyclopentyl and cyclohexyl. Examples of substituted cycloalkyl radicals are methylcyclopentyl and methylcyclohexyl.

Examples of alkyl substituents, which preferably contain 1–4 C atoms, are methyl, ethyl, n- and i-propyl and n-, i- and t-butyl.

Examples of alkoxy substituents, which preferably contain 1–4 C atoms, are methoxy, ethoxy, n-propoxy and t-butoxy.

Examples of dialkylamino substituents, in which the alkyl groups preferably contain 1–4 C atoms, are dimethylamino, diethylamino and di-n-propylamino.

Some examples of substituted phenyl and benzyl are 2,6-dimethylphen-4-yl, 2,6-diethylphen-4-yl, toluyl, p-methoxyphenyl and 2,6-dimethoxyphen-4-yl.

$R_1$ and $R_2$ are preferably unsubstituted $C_1$–$C_4$alkyl, phenyl or benzyl.

Preferred examples of $R_1$ and $R_2$ are methyl, ethyl, n-propyl, cyclopentyl, cyclohexyl, phenyl and benzyl.

$R_1$ and $R_2$ particularly preferably are identical and represent methyl. The compound is then 2,5-bis(thiomethyl)-1,4-tetracyanoquinodimethane, abbreviated to 2,5-DMeS-TCNQ below.

The invention also relates to a process for the preparation of compounds of the formula I, which comprises i) reacting a compound of the formula II

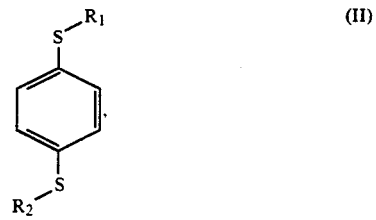

in which $R_1$ and $R_2$ are as defined above, with paraformaldehyde in the presence of concentrated HCl and $CH_3COOH$ to give a compound of the formula III

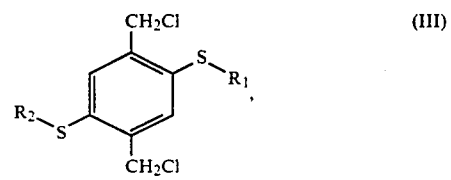

ii) converting this compound of the formula III into a compound of the formula IV

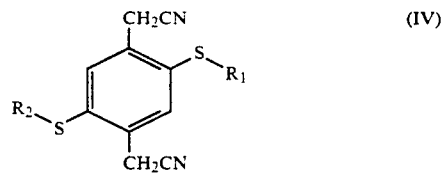

by reaction with NaCN, iii) subsequently converting this compound of the formula IV into a compound of the formula V

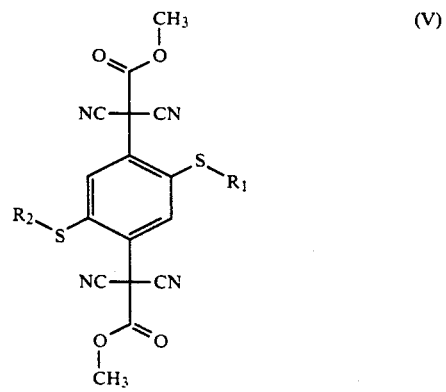

by reaction with $CH_3ONa$, $(CH_3O)_2CO$ and ClCN, and iv) dissolving this compound of the formula V in an aqueous base under an inert atmosphere and converting it into the compound of the formula I by the action of Br$_2$ and concentrated HCl.

The process is known per se and is described by R. C. Wheland and E. L. Martin in J. Org. Chem. Volume 40, No. 21, pages 3101–9 (1975).

The process for the preparation of the starting substances of the formula II is furthermore known per se, and is described by L. Engman et al. in J. Organometallic Chem., 296, pages 357–66 (1985).

Reaction stages i) and iv) can be carried out at a reaction temperature of between 40° and 110° C., preferably at 50° to 90° C.

Suitable solvents for reaction stage ii) can be polar and aprotic, and include, for example, the following: sulfones; sulfoxides; N,N'-tetrasubstituted ureas; N-alkylated lactams or N-dialkylated acid amides; ethers; aliphatic, cycloaliphatic or aromatic hydrocarbons, which can be substituted by F, Cl or C$_1$–C$_4$alkyl; carboxylic acid esters and lactones; and nitriles.

Examples are:

Sulfones: dimethyl sulfone, diethyl sulfone.

Sulfoxides: dimethyl sulfoxide (DMSO), diethyl sulfoxide.

N,N-Tetrasubstituted urea: N-methylethyl-N'-methylethylurea, tetramethylurea.

N-Alkylated lactams: N-methylpyrrolidone, N-ethylpyrrolidone.

N-Dialkylated acid amides: N-dimethylformamide, N-dimethylacetamide.

Ethers: diethylene glycol dimethyl ether, diethylene glycol diethyl ether.

Aliphatic hydrocarbons: hexane, heptane, nonane.

Cycloaliphatic hydrocarbons: decahydronaphthalene, methylcyclohexane.

Aromatic hydrocarbons: xylene, benzene, dichlorobenzene.

Carboxylic acid esters: methyl acetate, ethyl acetate.

Nitriles: benzonitrile, phenylacetonitrile, acetonitrile.

Preferred solvents are DMSO and dimethylformamide.

The NaCN can be added at 20° to 30° C., and when addition is complete, the temperature can be kept between 40° and 90° C.

In stage iii), CH$_3$ONa and (CH$_3$O)$_2$CO can be brought together with a compound of the formula IV, and reacted, for example, at 50° to 80° C. A solvent which forms an azeotrope with CH$_3$OH, for example benzene, may be added in order to distil off the methanol azeotrope formed. Thereafter, ClCN can be passed in at 0°–10° C., preferably 3° to 7° C., until the reaction is complete.

The last stage, iv), is advantageously carried out under an inert atmosphere, for example argon, the compound of the formula V first being dissolved in KOH or NaOH. The reaction with Br$_2$ and concentrated acid, for example HCl, is advantageously carried out at room temperature. Water-miscible solvents, for example methanol, ethanol, diethyl ether, tetrahydrofuran and dioxane, can additionally be used in this process stage.

The product of each stage can be isolated in a manner which is known per se, for example by decanting, filtration or distillation. The products can then be purified by means of customary methods, for example crystallisation or chromatographic methods.

The invention also relates to compounds of the formula III

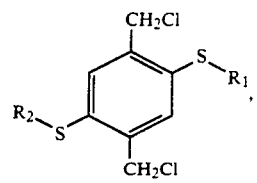

in which R$_1$ and R$_2$ are as defined above.

R$_1$ and R$_2$ are particularly preferably identical and represent methyl. The compound is then 1,4-bis(chloromethyl)-2,5-bis(thiomethyl)-benzene.

The compounds of the formula I are pi-acceptors and are not oxidised by air. As vapour-deposited layers, they exhibit electrical conductivities which correspond to those of semiconductors. Surprisingly, the compounds of the formula I according to the invention are in themselves organic semiconductors which are built up from only one component, and surprisingly do not change this property in contact with air.

The invention furthermore relates to a carrier material which contains a layer of at least one compound of the formula I on at least one surface.

Suitable carriers are, for example, metals, metal alloys, glasses, minerals, ceramics, thermosetting plastics and thermoplastics. Glasses, thermosetting plastics and thermoplastics are preferred. The carrier can be 0.01 mm to 1 cm, preferably 0.1 mm to 0.5 cm thick. Preferred carriers are glasses and homo- or copolymeric plastics. Suitable plastics are, for example, thermoplastic polycarbonates, polyamides, polyesters, polyacrylates and polymethacrylates, polyurethanes, polyolefins, polyvinyl chloride, polyvinylidene fluoride and polyimides, and thermosetting polyesters and epoxy resins.

The carriers can be prepared by the mixing and shaping processes customary for thermosetting plastics and thermoplastics, for example casting, pressing, injection moulding and extrusion processes.

One or more layers of an inert insulating material, for example plastics, can be applied as (an) intermediate layer(s) to the carrier, especially if the carrier is an electrically conductive material. The intermediate layers can also serve as adhesion promoters.

The layer thickness of the inert insulating material is, for example, 40 to 3000 Å, preferably 50 to 2000 Å.

One or more, for example 1 to 10, preferably 1 to 5, and particularly preferably 1 to 3 layers of compounds of the formula I can be applied to the carrier or the intermediate layer.

The layer thickness of the layer of compounds of the formula I is, for example, 100 to 3000 Å, preferably 100 or 2000 Å and particularly preferably 200 to 1500 Å.

A protective layer, for example of plastics, can be applied to the layer of compounds of the formula I.

Suitable coating processes are, for example, dipping, pouring, brushing, knife-coating, spin casting and vapour deposition processes, which are carried out under a high vacuum. If solvents are used, it should be ensured that the carriers used are insensitive toward these solvents. The layers are preferably produced by means of vapour deposition processes, in particular in vacuo. Suitable coating processes are described, for example, in EP-A-0 401 791.

Application of the layer(s) is preferably carried out by vapour deposition in vacuo. The material to be applied is first introduced into a suitable vessel, which is provided with resistance heating if appropriate, and is then placed in a vacuum chamber. The carrier on which the vapour is to be deposited is inserted in a holder above the vessel containing the material to be vapour-deposited. This holder is constructed such that the carrier can be rotated (for example at 10 revolutions per minute) and heated if appropriate. The vacuum chamber is evacuated to about $1.3 \times 10^{-5}$ to $1.3 \times 10^{-6}$ mbar ($10^{-5}$ to $10^{-6}$ mm Hg), and the heating is adjusted such that the temperature of the material to be vapour-deposited rises up to its vaporisation temperature. Vaporisation is continued until the vapour-deposited layer has the desired thickness.

The compounds of the formula I according to the invention form firmly adhering layers on the carrier materials. Owing to its semiconductor properties, the coated carrier material is outstandingly suitable for shielding from electrical and/or magnetic fields. The invention furthermore relates to the use of the coated material according to the invention as an antistatic packaging material.

The invention also relates to the use of the compounds of the formula I for antistatic finishing of objects.

The compounds of the formula I according to the invention can form charge transfer (CT) complexes with the following cations: for example Ag, Cu, Ni, alkali metals, for example Li, Na and K, alkaline earth metals, for example Mg, Ca and Sr, and other electron acceptors, for example tetrathiofulvalenes, tetrathiotetracenes, N-alkylpyridines, quinolines and ferrocenes. Similar CT complexes are described, for example, by I.A. Howard in Semiconductors and Semimetals, Volume 27, pages 29-85 (1988).

The following examples illustrate the invention in detail.

A. PREPARATION EXAMPLE

EXAMPLE A1 a) Preparation of 1,4-bis(chloromethyl)-2,5-bis(thiomethyl)-benzene

A suspension of 21.5 g (126 mmol) of 1,4-bis(thiomethyl)-benzene in a solution of 60 ml of HCl (37%) and 60 ml of CH$_3$COOH is heated in a hot oil bath at 100° C. At an internal temperature of 50° C., 19 g (633 mmol) of paraformaldehyde are added, and at an internal temperature of 65° C., gaseous HCl is passed through. The reaction mixture forms an emulsion at this temperature. The internal temperature increases to 85° C., and solid contents form after 30 minutes. HCl is passed through the reaction mixture during the next hour, with intensive stirring. The hot reaction mixture is then decanted off and washed with water. 100 ml of diethyl ether are added to the residue, the solid is filtered off and the resulting substance is washed with diethyl ether and then with water and dried in vacuo: yield 5.9 g (17.5%) of white crystals, melting point (m.p.): 189° to 189.5° C. MS (m/e): 266 (M$^+$, 100%), NMR (CDCl$_3$): 2.52 (3H, s), 4.73 (2H, s), 7.34 (2H, s).

b) Preparation of 1,4-bis(cyanomethyl)-2,5-bis(thiomethyl)-benzene 2.6 g (53 mmol) of NaCN are suspended in DMSO and the suspension is heated to 50° C., while stirring. Everything has dissolved after about 20 minutes. The heating bath is lowered in temperature and 5.9 g (22 mmol) of 1,4-bis(chloromethyl)-2,5-bis(thiomethyl)-benzene (Example A1a) are introduced in portions; the reaction is exothermic and the temperature is kept between 47° and 50° C. Duration of the introduction: 25 minutes. Thereafter, the mixture is subsequently stirred at 50° to 55° C. for 1 hour and at 85° C. for 10 minutes. After the heating, the mixture is cooled to 40° C. and the solution is poured into 350 ml of cold water. The resulting precipitate is filtered off with suction and washed neutral with water. The resulting product is rinsed with 50 ml of ethanol and dried. Yield: 5.5 g (100%) of white crystals, m.p.: 198° to 205° C. MS (m/e): (M$^+$, 100%), NMR (CDCl$_3$): 2.53 (3H, s), 3.83 (2H, s), 7.38 (2H, s).

c) Preparation of dimethyl $\alpha,\alpha,\alpha',\alpha'$-tetracyano-2,5-bis(thiomethyl)-1,4-phenylenediacetate 2.96 g (55 mmol) of freshly prepared CH$_3$ONa are added to a suspension of 5.5 g (22 mmol) of 1,4-bis(cyanomethyl)-2,5-bis(thiomethyl)-benzene (Example A1b) in 30 ml of dimethylcarbonate, while stirring thoroughly. The suspension is heated in a hot oil bath at 100° C. It becomes brown during this operation, and the starting substance dissolves and shortly thereafter precipitates again as a fine precipitate. 21 ml of benzene are added at 65° C., and the methanol formed is distilled off azeotropically. This operation is repeated four times within 2 hours. At the end, the boiling point is 78° C. The mixture is diluted again with 21 ml of benzene and the suspension is cooled to 5° C. with ice. Thereafter, 7.5 ml of previously condensed ClCN are passed in, whereupon a slightly exothermic reaction takes place. After the ClCN has been passed in, the ice bath is removed and the pale brown suspension is warmed to room temperature (RT). The suspension is then stirred at 70° C. for 2 hours. It is subsequently concentrated to dryness in vacuo. The residue is stirred with H$_2$O, decanted off, treated with fresh water several times, crystallised with ethanol, filtered off with suction, rinsed with fresh ethanol and dried. Yield: 4.4 g (47.9%) of white powder, m.p.: 172° to 177° C. MS (m/e): 414 (M$^+$, 61%), NMR (CDCl$_3$): 2.60 (3H, s), 4.06 (3H, s), 7.94 (2H, s).

d) Preparation of 2,5-bis(thiomethyl)tetracyanoquinodimethane (2,5-DMeS-TCNQ)

A suspension of 4.4 g (10.6 mmol) of dimethyl $\alpha,\alpha,\alpha',\alpha'$-tetracyano-2,5-bis(thiomethyl)-1,4-phenylenediacetate (Example A1c) in 25 ml of 10% KOH is heated under argon in an oil bath at 60° C. for 30 minutes, and then cooled to RT within 1 hour. The suspension is filtered off with suction and the red-brown filtrate is added to a solution of 15 ml of concentrated HCl in 10 ml of water, while cooling, whereupon a pale beige precipitate forms. A solution of 2.1 g (13 mmol) of Br$_2$ in 110 ml of water is added to this suspension. The dark brown-black suspension present is filtered off with suction after 15 minutes and washed with water. After repeated washing with 80 ml of ethanol and 80 ml of acetone, the crude product is dissolved hot in 2.5 l of CH$_2$Cl$_2$ and the solution is then evaporated to a volume of 600 ml. The dark green solution is filtered over 700 g of silica gel using CH$_2$Cl$_2$. The crude product is sublimed in a quartz tube at an oven temperature of 210° to 215° C. under a vacuum of $10^{-2}$ mbar. Yield: 1.24 g (39.6%) of gold-brown crystals, m.p.: 305.4° C. MS (m/e): 296 (M$^+$, 79%), NMR (CDCl$_3$): 2.64 (3H, s), 7.02 (2H, s).

B. USE EXAMPLES

EXAMPLE B1

Conductivity Measurements

A thin 100 Å layer of SiO$_2$ followed by a thin 380±40 Å layer of 2,5-DMeS-TNCQ are deposited on a glass substrate. Four gold strips 0.6 mm wide are applied to the conductive layer at a distance of 1 mm with the aid of a vapour-deposition mask. A specific conductivity of $\sigma = 1.9 \times 10^{-5}$ S/cm is determined with this sample structure. The TCNQ(OEt)(SMe) described by R. Wheland et al. in J. Org. Chem. 10, No. 21, page 3101 (1975) shows a conductivity of $\sigma = 1.8 \times 10^{-7}$ S/cm under identical conditions.

Measurement of the Surface Discharge

The surface discharge of about 200 V is formed with the aid of a gold-coated tungsten wire of 50 micrometer diameter, which is charged with a voltage of approximately 3.4 kV at an atmospheric humidity of 1.3%. This voltage is regulated such that the current is kept constant at 200 nA per cm of wire length. The sample is glued to a glass carrier with silver paste and connected electrically with a contact tip on the edge of the carrier. During the course of a measurement, the carrier shifts 8 mm under the corona wire at a speed of about 50 cm/s, and stops at the point where the contact tip dips into an earthed conductive foam. The sample then lies under a field meter (Isoprobe Electrostatic Voltmeter 244, Monroe Electronics Inc.). The voltage of the vapour-deposited layer is measured 5 seconds after the corona charging, and shows a value of 2±1 volt.

Transmittance Measurements

The transmittance of the vapour-deposited layer, measured in the range of 300-900 nm, is greater than 43%.

EXAMPLE B2

A thin 570±40 Å layer of 2,5-DMeS-TCNQ is vapour-deposited onto a polyester film. The specific conductivity, measured as described in Example 1, is $10^{-6}$ S/cm. The voltage of this vapour-deposited layer is measured 5 seconds after corona charging and shows a value of 2±1 volt.

EXAMPLE B3

2,5-DMeS-TCNQ as an electron acceptor for the preparation of organic metals 8 mg of 2,5-DMeS-TCNQ and 40 mg of AgBF$_4$ are electrolysed in 3 ml of CH$_3$CN for 30 days at a current strength of 2 μA in a 5 ml capacity electrolysis cell equipped with two 0.5 mm φ Pt electrodes (distance between the electrodes: 2 cm). The 0.5 mm long dark-blue needles deposited on the cathode have a conductivity of about $\sigma = 2 \times 10^{-3}$ S/cm. The formula of this CT complex can be described generally as Ag$_x$(2,5-DMeS-TCNQ).

What is claimed is:

1. A compound of the formula I

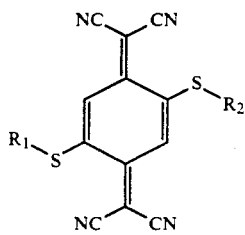

in which R$_1$ and R$_2$ independently of one another are C$_1$-C$_6$alkyl, C$_3$-C$_8$cycloalkyl which is unsubstituted or substituted by C$_1$-C$_4$alkyl, unsubstituted phenyl or benzyl, or phenyl or benzyl which is substituted by F, Cl, Br, C$_1$-C$_6$alkyl, C$_1$-C$_6$alkoxy or di(C$_1$-C$_6$alkyl)amino.

2. A compound of the formula I according to claim 1, in which R$_1$ and R$_2$ are identical.

3. A compound of the formula I according to claim 1, in which R$_1$ and R$_2$ independently of one another are C$_1$-C$_4$alkyl.

4. A compound of the formula I according to claim 1, in which R$_1$ and R$_2$ are methyl, ethyl, n-propyl, cyclopentyl, cyclohexyl, phenyl or benzyl.

5. A compound of the formula I according to claim 1, which is 2,5-bis(thiomethyl)-tetracyanoquinodimethane.

* * * * *